United States Patent
Meyer

(10) Patent No.: US 12,036,415 B2
(45) Date of Patent: Jul. 16, 2024

(54) TECHNIQUES FOR HEART MUSCLE REMODELING USING A CARDIAC PACEMAKER AND RELATED SYSTEMS AND METHODS

(71) Applicant: The University of Vermont and State Agricultural College, Burlington, VT (US)

(72) Inventor: Markus Meyer, Arden Hills, MN (US)

(73) Assignee: The University of Vermont and State Agricultural College, Burlington, VT (US)

( * ) Notice: Subject to any disclaimer, the term of this patent is extended or adjusted under 35 U.S.C. 154(b) by 119 days.

(21) Appl. No.: 17/665,382

(22) Filed: Feb. 4, 2022

(65) Prior Publication Data

US 2022/0203100 A1    Jun. 30, 2022

Related U.S. Application Data

(63) Continuation of application No. 16/339,315, filed as application No. PCT/US2017/055536 on Oct. 6, 2017, now Pat. No. 11,260,233.

(Continued)

(51) Int. Cl.
  *A61N 1/365*  (2006.01)
  *A61N 1/362*  (2006.01)
  *A61N 1/02*   (2006.01)

(52) U.S. Cl.
  CPC ....... *A61N 1/36542* (2013.01); *A61N 1/3627* (2013.01); *A61N 1/36585* (2013.01); *A61N 1/025* (2013.01)

(58) Field of Classification Search
  CPC .................. A61N 1/3627; A61N 1/362; A61N 1/36542
  See application file for complete search history.

(56) References Cited

U.S. PATENT DOCUMENTS 4,782,836 A   11/1988  Alt
5,833,713 A   11/1998  Moberg
(Continued)

FOREIGN PATENT DOCUMENTS

CN   104023788 A   9/2014
CN   105163803 A   12/2015
(Continued)

OTHER PUBLICATIONS

Extended European Search Report for European Application No. 17859259.8, dated May 27, 2020.

(Continued)

*Primary Examiner* — George R Evanisko
(74) *Attorney, Agent, or Firm* — Wolf, Greenfield & Sacks, P.C.

(57) ABSTRACT

According to some aspects, a cardiac pacemaker for implantation within a subject is provided, the pacemaker including a housing, at least one sensor configured to detect an activity level of the subject, and at least one processor coupled to the sensor configured to detect inactivity of the subject based on output from the at least one sensor, produce a first signal configured to increase the heart rate of the subject to a first heart rate during a first time period, wherein the first heart rate is above a resting heart rate and below 100 beats per minute, and in response to determining that the first time period has elapsed, producing a second signal configured to increase the heart rate of the subject to a second heart rate during a second time period, wherein the second heart rate is between 100 and 140 beats per minute.

13 Claims, 5 Drawing Sheets

Related U.S. Application Data

(60) Provisional application No. 62/404,908, filed on Oct. 6, 2016.

(56) References Cited

U.S. PATENT DOCUMENTS

| | | | |
|---|---|---|---|
| 6,904,320 B2 | 6/2005 | Park et al. | |
| 7,133,718 B2 | 11/2006 | Bakken et al. | |
| 8,019,416 B2* | 9/2011 | Pastore | A61N 1/36564 607/9 |
| 8,380,309 B2 | 2/2013 | Bruns | |
| 11,260,233 B2* | 3/2022 | Meyer | A61N 1/36585 |
| 2004/0260348 A1* | 12/2004 | Bakken | A61N 1/365 607/9 |
| 2005/0076908 A1 | 4/2005 | Lee et al. | |
| 2005/0137631 A1* | 6/2005 | Yu | A61N 1/365 607/9 |
| 2008/0114408 A1 | 5/2008 | Shuros et al. | |
| 2015/0051660 A1* | 2/2015 | Meyer | A61N 1/36535 607/18 |
| 2020/0038663 A1 | 2/2020 | Meyer | |

FOREIGN PATENT DOCUMENTS

| | | |
|---|---|---|
| JP | 2007-524450 A | 8/2007 |
| JP | 2010-512958 A1 | 4/2010 |
| WO | WO 2013/148182 A1 | 10/2013 |

OTHER PUBLICATIONS

International Search Report and Written Opinion for International Application No. PCT/US2017/055536, dated Dec. 1, 2017.
International Preliminary Report on Patentability for International Application No. PCT/US2017/055536, dated Apr. 18, 2019.

* cited by examiner

TECHNIQUES FOR HEART MUSCLE REMODELING USING A CARDIAC PACEMAKER AND RELATED SYSTEMS AND METHODS

CROSS-REFERENCE OF RELATED APPLICATIONS

This application claims the benefit under 35 U.S.C. § 120 as a continuation of U.S. application Ser. No. 16/339,315, filed Apr. 3, 2019, which is a national stage filing under 35 U.S.C. § 371 of International Patent Application Serial No. PCT/US2017/055536, filed Oct. 6, 2017, which claims priority to U.S. Application Ser. No. 62/404,908, filed Oct. 6, 2016. The entire contents of these applications are incorporated herein by reference in their entirety.

BACKGROUND

It is known that individuals having a sedentary lifestyle and lacking in exercise typically have more cardiac-related health problems than active individuals. A sedentary lifestyle can lead to a reduction in the size of the heart's main chambers. This can also occur as an effect of prolonged hypertension that increases the muscle thickness, thereby reducing heart chamber size. Irrespective of its cause, a decrease in cardiac chamber volumes reduces the stroke volume, which can affect the cardiac output of the heart. A limitation in cardiac output greatly reduces the ability to exercise.

Heart failure with preserved ejection fraction (HFpEF) is now the most frequent cause of heart failure. HFpEF is frequently associated with hypertension (HTN), concentric left ventricular hypertrophy (LVH), a reduced left ventricle (LV) chamber size and increased LV stiffness. Impaired LV filling and small chamber size reduce the functional capacity through a limitation of cardiac output reserve.

SUMMARY

According to some aspects, a cardiac pacemaker for implantation within a subject is provided, the pacemaker comprising a housing, at least one sensor configured to detect an activity level of the subject, and at least one processor inside the housing and coupled to the sensor, the at least one processor configured to stimulate a remodeling of the subject's heart muscle through modulation of the subject's heart rate by detecting inactivity of the subject based on output from the at least one sensor, when said inactivity of the subject is detected, producing a first signal configured to increase the heart rate of the subject to a first heart rate during a first time period, wherein the first heart rate is above a resting heart rate and below 100 beats per minute, and in response to determining that the first time period has elapsed, producing a second signal configured to increase the heart rate of the subject to a second heart rate during a second time period, wherein the second heart rate is between 100 and 140 beats per minute.

According to some embodiments, the at least one sensor includes a motion detector.

According to some embodiments, the at least one processor is further configured to stop producing the first signal or the second signal when activity of the subject is detected based on output from the at least one sensor.

According to some embodiments, the second heart rate is based at least in part on the subject's height, weight and/or gender.

According to some embodiments, the first heart rate is above 90 beats per minute and below 100 beats per minute.

According to some embodiments, the second signal is produced in response to determining, by the at least one processor, that the second signal has not been produced within a prior number of hours.

According to some embodiments, the prior number of hours is six hours.

According to some embodiments, the first time period is a time period having a length of at least two minutes and less than ten minutes.

According to some embodiments, the first time period is a time period of approximately five minutes.

According to some embodiments, the second time period is a time period having a length of at least thirty minutes and less than two hours.

According to some embodiments, the second time period is a time period of approximately one hour.

According to some embodiments, the second heart rate is between 110 and 140 beats per minute.

According to some aspects, a method is provided comprising, using at least one processor, detecting inactivity of a subject based on output from at least one sensor, when said inactivity of the subject is detected, producing a first signal configured to increase the subject's heart rate to a first heart rate during a first time period, wherein the first heart rate is above a resting heart rate and below 100 beats per minute, and in response to determining that the first time period has elapsed, producing a second signal configured to increase the subject's heart rate to a second heart rate during a second time period, wherein the second heart rate is between 100 and 140 beats per minute.

According to some embodiments, the subject is not otherwise indicated for a currently accepted treatment with a pacemaker.

According to some embodiments, the subject is obese.

According to some embodiments, the subject has high blood pressure and/or heart failure with preserved ejection fraction or an impaired ability to relax the heart muscle.

According to some embodiments, detecting said inactivity of the subject comprises detecting that the subject is sleeping.

According to some embodiments, the second heart rate is based at least in part on the subject's height, weight and/or gender.

According to some embodiments, the second signal is produced in response to determining, by the at least one processor, that the second signal has not been produced within a prior number of hours.

According to some embodiments, the prior number of hours is six hours.

According to some embodiments, the second heart rate is between 110 and 140 beats per minute.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

DETAILED DESCRIPTION

Figure 1:
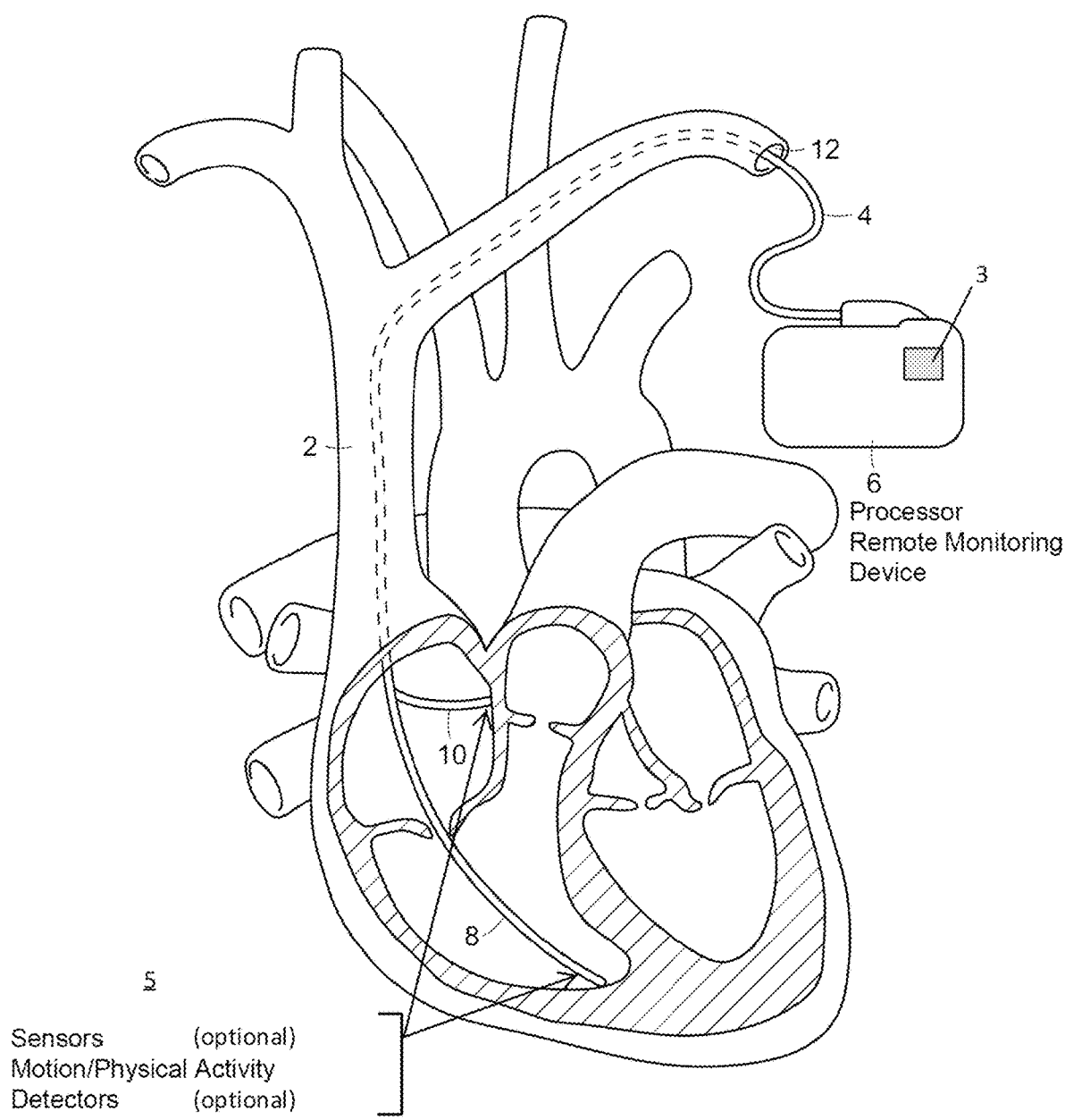
FIG. 1 depicts a cardiac pacemaker implanted in a body with a wire extending into the heart, according to some embodiments.

An increase in heart rate to above normal resting rates can enlarge the heart. If the heart rate is very elevated and/or elevated for prolonged times a subject can develop enlarged heart chambers and/or heart failure. This is a clinical phenotype commonly called tachycardia induced cardiomyopathy. If, alternatively, the heart rate is moderately or intermittently elevated, the enlargement of the chamber can be beneficial. For example, endurance athletes such as professional cyclists can increase their chamber sizes to levels that are considered to be enlarged. This allows them to increase cardiac output to exceptional levels, increasing their exercise capacity to supra-physiological levels. Because these changes can regress with inactivity they are considered to be benign and are called athlete's heart. However, subjects who develop atrial fibrillation with uncontrolled rapid ventricular conduction can also develop a similar enlargement of their heart chamber volumes. If the heart rate is uncontrolled for prolonged times it can result in tachycardia induced cardiomyopathy. Restoration of the heart rate to normal levels with or without medications can quickly normalize the size of the heart chambers.

In general, myocardial tissue has plasticity and is capable of remodeling. Myocardium also rapidly adapts to a change in circulatory demands, such as in hypertension-induced thickening of the heart muscle, often referred to as left ventricular hypertrophy (LVH). Heart rate (HR) also affects myocardial remodeling. Increased HRs with endurance exercise and during pregnancy contribute to an LV chamber enlargement of up to twice the normal size. This type of LV remodeling is benign and reversible.

LV chamber expansion without increase in LV mass can also be induced in animals through tachycardia pacing. This phenotype also quickly reverses upon restoration of a normal heart rate. Tachycardia-induced LV chamber enlargement is also seen in subjects after atrial fibrillation associated ventricular tachycardia. In this setting it is assumed that restoration of normal ventricular rates would be sufficient to reduce LV chamber size.

The inventor has recognized and appreciated techniques to produce myocardial pacing-induced LV remodeling. In particular, a symptomatic improvement of a subject with HFpEF after atrial fibrillation with rapid ventricular conduction that restored normal LV chamber dimensions and improved diastolic function has been observed after the ventricular rate was controlled. The inventor has recognized and appreciate techniques to realize such an improvement by configuring a pacemaker to increase a subject's heart rate during periods of inactivity, rather than the conventional adjustments performed during periods of activity. As a result, beneficial remodeling of the subject's heart may be produced. For instance, the subject's heart rate may be increased while the subject is asleep to a level sufficient to produce beneficial enlargements to the subject's heart chamber(s). This increase may mimic one or more physiological aspects of exercise, and thereby condition the heart muscle.

The inventor has further recognized and appreciated a particular range of heart rates that, when a subject's heart rate is raised to within this range, can safely produce beneficial changes to the subject's heart chamber(s) (e.g., increase their volume) without producing discomfort in the subject. Specifically, heart rates above 100 beats per minute (bpm) and below 140 bpm have been observed to produce physiological effects such as mild-to-moderate reduction in blood pressure, a reduction in left ventricular end-diastolic pressure (LVEDP), higher caloric utilization, or combinations thereof. Heart rates within this window have also been found not to cause substantial discomfort in a subject when applied during periods of inactivity of the subject, such as sleep or other situations in which limited motion occurs.

According to some embodiments, a pacemaker fitted to a subject may be configured to increase the subject's heart rate to a rate within the 101 bpm to 140 bpm window once it has been determined that the subject is inactive (101 bpm is used herein merely for clarity to refer to a lower bound on the heart rate that is above 100 bpm, but any heart rate above 100 bpm, such as 100.5 bpm could equivalently be utilized). In some implementations, the pacemaker may be configured with one or more sensors that detect a level of activity of the subject, such as a heart rate monitor and/or a motion detector (e.g., accelerometer). After first ascertaining that the subject is inactive, the heart rate may be gradually ramped up to the target heart rate and held at or close to the target rate for a predetermined duration.

According to some embodiments, the pacemaker may be configured to stop increasing the heart rate of the subject (e.g., stop producing instructions and/or a signal that cause the pacemaker to attempt to adjust the heart rate) when it is determined that the subject has raised their activity level above some threshold. As such, the pacemaker may be configured to periodically determine the activity level during a period in which the pacemaker is increasing the heart rate. This feature may be provided for safety so that the heart rate of the subject does not raise to dangerous levels due to the combination of artificial stimulus designed to produced remodeling effects and cardiac activity caused by physical activity of the subject.

According to some embodiments, a pacemaker may be configured to raise a subject's heart rate to above a resting heart rate yet below the 101 bpm to 140 bpm window discussed above for a period prior to raising the heart rate to within the 101 bpm to 140 bpm window. The inventor has recognized and appreciated that there may be physiological benefits to performing a comparatively short initial increase in the heart rate prior to increasing the heart rate into the 101 bpm to 140 bpm that, as discussed above, may cause beneficial hemodynamic effects and/or remodeling of the heart chamber(s). These additional benefits may include a reduction in blood pressure, reduced incidence of atrial fibrillation, fewer and/or less severe symptoms of heart failure, a reduction in left atrial pressures and/or left ventricular end-diastolic pressure (LVEDP), higher caloric utilization, or combinations thereof. Moreover, this initial increase, referred to herein as an "interstitial remodeling stimulus," may produce changes to the heart at an interstitial and/or molecular level that may be, at least in some subjects, difficult to quantify. This initial stimulus forces the interstitium to remodel in order to allow an increase in chamber size thereby reducing tissue stiffness. This was recently demonstrated in a pig model of tachycardia.

According to some embodiments, a pacemaker fitted to a subject may be configured to increase the subject's heart rate to a rate within the 101 bpm to 140 bpm window no more than a particular number of times within a given time window. For instance, no more than once during successive six hour time windows (e.g., no more than once during each of 6 am-12 pm, 12 pm-6 pm, 6 pm-12 am and 12 am-6 am). The pacemaker may be configured to retain a log on previous operations to raise the subject's heart rate into the 101 bpm to 140 bpm window that were performed (e.g., times, durations, etc.) so that the log may be referred to when determining whether to initiate another such operation. Rules that describe how frequently and for how long such operation may also be referred to in such a determination.

According to some embodiments, a pacemaker fitted to a subject may be configured to increase the subject's heart rate to a level only slight elevated above a physiological resting heart rate. For example, a pacemaker fitted to a subject who has a resting heart rate of 60 bpm may be configured to increase the subject's heart rate to 70 bpm. The inventor has determined that lower heart rates increase the filling volume of the heart chambers, which will increase the blood pressures within the heart. This consequently may result in higher central blood pressures for lower heart rates, and in at least some cases may lead to problems such as atrial fibrillation. Increasing the subject's heart rate above resting may mitigate such problems by reducing the central blood pressure. In some cases, such an increase may be applied subsequent to a period in which the subject's heart rate is raised to a rate within the 101 bpm to 140 bpm window. For instance, when such a period ends (e.g. due to the period expiring or due to activity of the subject being detected), instead of the pacemaker allowing the heart rate to then drop to its resting rate, the pacemaker may instead be configured to drop the heart rate to a rate just above the resting rate.

A pacemaker uses low-energy electrical pulses to stimulate the heart and change the rate at which the heart beats. Generally speaking, when the techniques described herein are applied to a pacemaker, the pacemaker causes a slow or natural heart rhythm, also referred to as a "resting heart rate," to increase. A "resting heart rate" as used herein refers to a heart rate that is within a range associated with a subject at rest, such as a subject that is asleep. A normal resting heart rate is in the range from 40-90 beats per minute, and may vary between subjects and over time (e.g., as a given subject's body changes). Where a pacemaker is herein referred to as "increasing" a heart rate to a target rate (or otherwise altering the heart rate to a target rate), this refers to the pacemaker generating electrical signals intended to stimulate the heart and cause the heart's rate to change to this target rate.

The techniques described herein utilize a pacemaker programmed to increase the heart rate to a level greater than a normal resting heart rate. In some embodiments, it may be desirable for one or more sensors coupled to a processor of the pacemaker to be integrated into a feedback loop that controls pacing.

Some pacemakers may include other functionalities such as a position detector, a night function, and/or a remote monitoring device. Some pacemakers can also monitor blood temperature, breathing rate, and other factors and adjust your heart rate to these changes. A night function feature in a pacemaker involves the control of the base rate using at least one sensor that can monitor a physiological parameter. Different phases such as rest phase and resumption of activity phase are detected by the sensor and send a signal to adapt the base rate of the pacemaker accordingly. The base rate is allowed to increase above the normally programmed resting rate or base rate in response to actual rest of a subject, to encourage a rapid cardiac rhythm to stimulate the heart muscle.

Cardiac electrical activity and pacemaker function may be monitored remotely in some instances. For instance medical personnel can remotely monitor the pacing and adjust the pacing levels to increased levels when a subject is at rest. Another pacemaker feature is a rate adaptive pacemaker. These devices include a mechanism for determining the demand of the subject, a pacing rate controlling element for controlling the pacing rate in response to the subject's demand, and a pacing rate limiting mechanism for preventing the pacing rate from becoming too low.

The methods of the invention may be performed in a subject. A subject, as discussed herein, refers to a human or non-human vertebrate, but is preferably a human. Preferably the human is a subject in need of increasing the cardiac output reserve. For instance, such a subject may have a smaller than normal heart volume. In some instances the subject may already be using a pacemaker or may have other disease indications that call for the use of a pacemaker. In this case the pacemaker can be programmed to perform the methods of the invention.

In other embodiments, the subject may not be otherwise indicated for a currently accepted treatment with a pacemaker. For instance, the subject may be an obese subject. Alternatively or additionally, the subject may have high blood pressure and/or heart failure with preserved ejection fraction. Such a subject may not normally be fitted with a pacemaker due to health risks associated with increasing the heart rate during activity for such subjects. The techniques described herein may, however, be utilized with such subjects since the increased heart rate is applied during periods of inactivity, not activity, and consequently the same risks may not be present.

A subject more typically in need of treatment with a pacemaker is a subject predisposed to developing cardiac problems, such as for instance, a subject having one or more of the following characteristics: Decreased venous blood return, most commonly resulting from reduced blood volume (e.g., hemorrhage) or gravity causing blood to pool in the lower limbs when standing upright; Ventricular diastolic failure (decreased ventricular compliance) caused, for example, by ventricular hypertrophy or impaired relaxation (lusitropy) or Inflow (mitral and tricuspid) valve stenosis, which reduces ventricular filling.

A subject in need of treatment with a pacemaker of the invention may also include, but is not limited to, subjects with predispositions to cardiac problems, heart conditions associated with decreasing cardiac chamber sizes and associated heart dysfunction, decreased heart chamber size: Cardiomyopathy, high blood pressure, a subject having an injury or in circumstances where a subject's ability to exercise is impaired. Examples of factors associated with higher risk of cardiovascular disease include but are not limited to HIV, Diabetes, Coronary artery disease, high blood pressure, cardiomyopathy, atherosclerosis, disability, bedridden, air pollution, genetic history or family history of heart failure, high levels of cholesterol, obesity, alcohol, cocaine, smoking or the use of other drugs toxic to the heart (treatment of cancer), autoimmune diseases which have destroyed healthy body tissue and infections involving heart muscles.

Examples of biomarkers which may reflect a higher risk of cardiovascular disease include but are not limited to coronary artery calcification, carotid intima-media thickness, carotid total plaque area, higher fibrinogen and PAI-1 blood concentrations, elevated homocysteine, elevated blood levels of asymmetric dimethylarginine, inflammation as measured by C-reactive protein, elevated blood levels of brain natriuretic peptide (also known as B-type) (BNP).

As described in the Examples section, a study designed to analyze the feasibility of pacing-mediated LV remodeling was performed in a porcine model. This proof-of-concept study includes control animals with a normal blood pressure (no HTN) and hypertensive LVH animals (HTN/LVH) induced by unilateral renal artery steno sis (2K1C model) to demonstrate that pacing-mediated LV remodeling can be accomplished in the typical spectrum of normal EF phenotypes. The effect of low and moderate level tachycardia on LV geometry and function will be studied longitudinally to provide insights into the necessary HR requirements. The experimental design will allow for within and between group comparisons. Beneficial effects on diastolic function may be demonstrated in HTN/LVH animals in a 9 week survival study. This time may be necessary to develop a phenotype and study the effects of pacing-mediated LV remodeling.

Pacemakers can provide for heart rates observed in atrial fibrillation. According to some embodiments, pacemakers may also provide the same effect in a subject with small chamber volumes. The resulting increase in chamber size may allow the subject to exercise more and reduce symptoms.

Provided herein are methods and devices for performing normalizing heart chamber volumes in a subject. Heart chamber volumes are well known to the skilled artisan. A subject having a small heart chamber volume is one that has a lower than normal cardiac output. Such a subject may be diagnosed as having a small heart chamber volume based on echocardiography or any other cardiac imaging modality, cardiac output, symptoms such as shortness of breath or other means known to the skilled physician.

FIG. 1 illustrates a pacemaker device configured as described herein in the context of a heart, according to some embodiments. In the example of FIG. 1, a pacemaker 6 having a wire 4 extending therefrom is shown. The wire 4 extends through the subclavian vein 12 and past the superior vena cava 2 in the example. The wire optionally splits into a wire to the right atrium 10 and a wire to the right ventricle 8. The sensors or electrodes typically detect electrical activity in the heart and send data through the wires to the processor in the pacemaker. If the heart rhythm detected via the received data represents a resting heart rhythm, the processor will direct the pacemaker to send electrical pulses to the heart. The pulses then travel through the wires to reach heart, where the heart is stimulated to increase heart rate.

A cardiac pacemaker as described herein is a self-contained unit that sends electrical stimulation to the heart. Typically, a pacemaker is implanted into a subject to alleviate symptoms of decreased cardiac output related to an abnormally low heart rate and/or rhythm. Pacemakers are generally used for persistent, symptomatic second- or third-degree atrioventricular (AV) block and symptomatic sinus and atrial bradycardia. While the methods of the invention may be accomplished using standard pacemakers known in the art, the techniques described herein utilize a pacemaker programmed to perform a different function—that is, to increase heart rate at certain times in response to determining that the subject is inactive. Pacemakers have been described in for instance: US2001012954A, U.S. Pat. Nos. 4,688,573A, 4,803,987A, 5,467,773A, 3,885,552A, 5,694,940A, 6,485,416B, 3,885,552A, 4,567,892A each of which is incorporated by reference.

A pacemaker may comprise a number of pacemaker components, such as an analog commutator, area amplifier, peak amplitude amplifier, pulse width-hold control circuit, pacer pulse selector, pacer pulse amplifier, ECG amplifier, high speed electro-cardiogram ECG preamplifier, control logic system, VCO audio system, or combinations thereof. The pacemaker may be configured to make various determinations and calculations as described herein, which may be via a processor and software within a pacemaker, and/or via circuitry of the pacemaker, as the techniques described herein are not limited to any particular combination of hardware and/or software used by the pacemaker. A processor as referred to herein may include a general purpose processor programmed to perform recited functions, and/or may include a custom-built processor (e.g., an ASIC). In some implementations, the pacemaker may include volatile and/or non-volatile memory that can store data, such as sensor data and/or data used in calculating an activity level of a subject.

According to some embodiments, the pacemaker 6 may include one or more sensors 3 configured to obtain sensor data relating to the subject's activity level. These may be supplied in addition to, or alternatively to, the optional sensors and/or motion/physical activity detectors 5 shown in FIG. 1. As a non-limiting list, sensor(s) 3 may include a number of: an oxygen saturation sensor, a venous pH sensor, a QT interval detector, a motion sensor (e.g., accelerometer), a respiratory minute volume (MV) sensor, a stroke volume sensor, a central venous temperature sensor, a minute ventilation sensor, a peak endocardial acceleration sensor, a right ventricular impedance during cardiac cycle sensor, or combinations thereof. The pacemaker 6 may be coupled to the one or more sensors and may estimate an activity level of the subject based on sensor data received from the one or more sensors. In making such an estimation, the pacemaker may analyze sensor data from a prior window of time, such as the past 5 seconds, the past 10 seconds, etc. Moreover, the pacemaker may access data used to interpret the sensor data and, where multiple sensors are used, with data used to combine sensor inputs to make the estimation of activity level.

It will be appreciated that the example of FIG. 1 does not necessarily depict components of sensor(s) 3 that may be present in order to gather the relevant sensor data. For instance, a venous pH detector might incorporate some mechanism to obtain a sample of the subject's blood and determine a pH level of the blood. For clarity, possible components for the non-limiting list of sensor technologies described above are not shown in the figure, but may, according to some embodiments, be present in the system of FIG. 1.

In some embodiments, the pacemaker 6 may be a single-chamber pacemaker in which only one pacing lead is placed into a chamber of the heart—either the atrium or the ventricle. In other embodiments, the pacemaker may be a dual-chamber pacemaker in which leads are placed in two chambers of the heart. One lead paces the atrium and one lead paces the ventricle. The dual-chamber type more closely resembles the natural pacing of the heart by assisting the heart in coordinating the function between the atria and ventricles.

In some embodiments, a cardiac pacemaker system may comprise a battery, a computerized generator or processor, and wires (leads) with sensors sometimes referred to as electrodes on one end. The battery and the generator/processor may be located within or outside of the housing 6. The battery powers the generator/processor. The wires extend from the housing and connect the generator to the heart.

Figure 2:
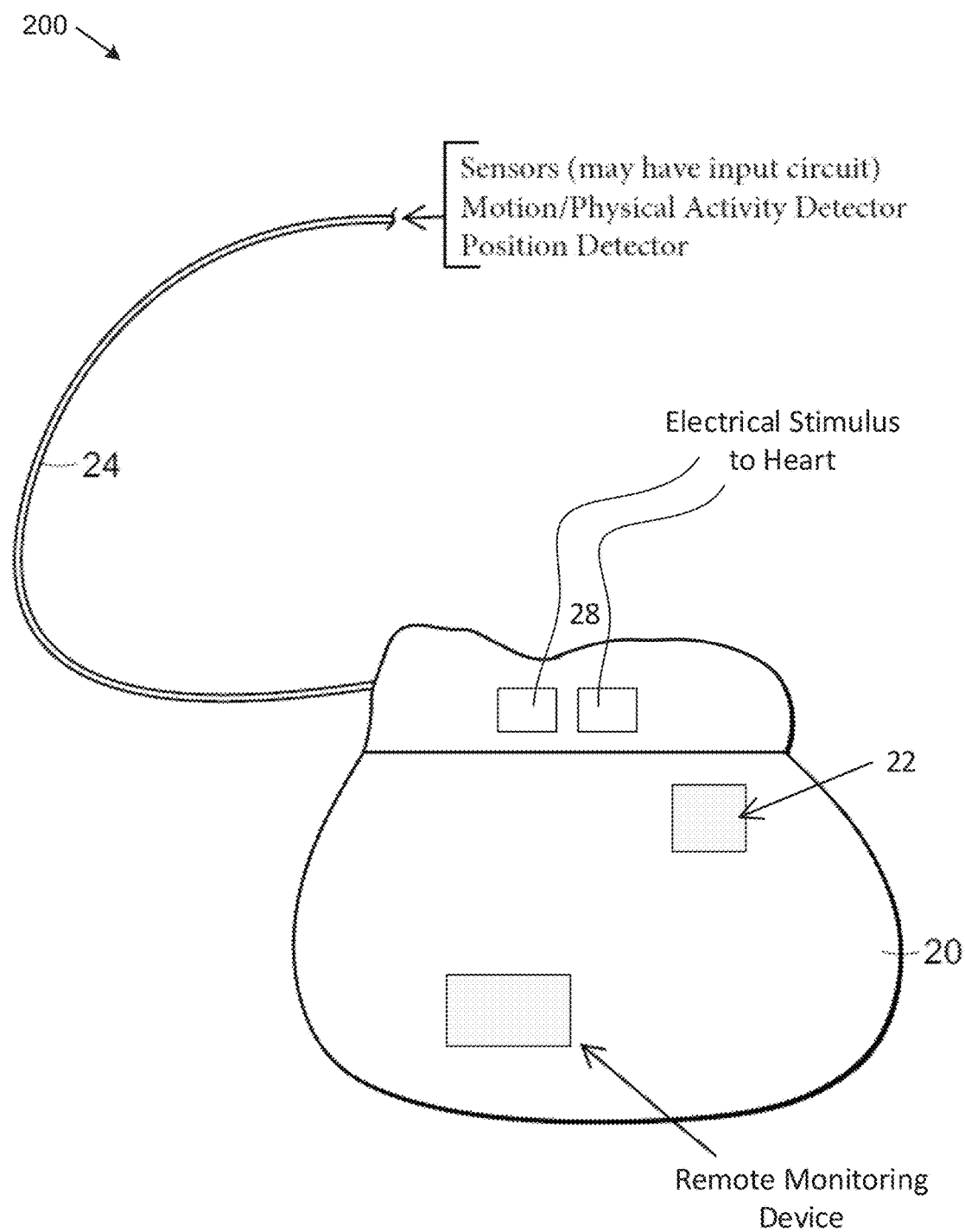
FIG. 2 illustrates details of a cardiac pacemaker, according to some embodiments.

An illustrative cardiac pacemaker is shown in FIG. 2. A sensor in the form of a wire 24 extends from the housing 20. The housing includes one or more processors 22. The sensor may be implanted into a subjects heart and may include any number and type of sensors, examples of which are provided above. The sensor wire can be split such that it interacts with multiple chambers of the heart, or it may simply interact with one chamber. The sensor(s) detect the heart rate and send a signal to a processor 22 in the pacemaker. Thus, the sensor may have an input circuit that receives a signal representative of a heartbeat sensed within a heart as a function of time. When a resting or otherwise inactive heart rate is detected an output signal is produced by processor 22 and output via electrodes 28 to the heart. The output signal may be configured to stimulate the heart to increase the heart rate over the resting heart rate level. In the example of FIG. 2, the pacemaker 20 also includes a remote monitoring device.

The subject may be stimulated to have an increased heart rate for any amount of time. The amount of time that the heart rate is increased may be predetermined. For instance the device may be set to produce an increase in heart rate for at least 5, 10, 15, 30, or 60 minutes or longer.

According to some embodiments, the processor of pacemaker 6 may be configured to stop sending a signal to increase heart rate upon detection of physical activity of the subject. Such detection may be based on one or more signals from sensor(s) 3 and/or sensors and/or motion/physical activity detectors 5. For instance, if the subject were to get up from rest, a sensor may sense movement by the subject, and sensor data input to the processor would cause the processor to stop sending the electrical signal that led to an increased heart activity.

The pacemaker 20 may in some embodiments be programmed to be responsive to the position or movement of the body. For instance the pacemaker may include sensors and/or may be coupled to external sensors that detect changes in the subject's physical activity and automatically adjust the pacing rate to achieve a normal heart rate. For example, if the pacemaker is set to pace at a higher than resting heart rate at night while the subject is asleep, if the sensor detects movement suggesting the subject is awake and moving around the rate may be reduced to a resting level. If the subject stops the movement for a period of time, such as 5 minutes, then the pacemaker may again provide a rate that is higher than the resting rate.

A cardiac pacemaker may also comprise a control device including a position detector connected to a movement sensor, wherein the position detector has a classification device for recognizing short movements. This type of sensor may also be used to detect motion or position that would trigger the pacemaker to operate at a resting rate.

The pacemaker may include a feedback sensor, such that when a low heart rate is detected the rate of the stimulation will be increased. Pacemaker 6 may be a temporary or a permanent pacemaker, both of which are useful according to the techniques described herein.

As discussed above, the techniques described herein relate to adjustment of a subject's heart rate by a suitable programmed pacemaker subsequent to detecting inactivity of the subject. These techniques utilize one or more mechanisms to detect inactivity and one or more mechanisms to produce a signal that cause electrical stimulation of the heart. Whilst these techniques are not limited to any particular arrangement of these mechanisms, nor their arrangement with respect to any components of a pacemaker, as examples, FIGS. 3A-C depict some illustrative arrangements of elements that may be used to practice the techniques described herein.

Figure 3A:
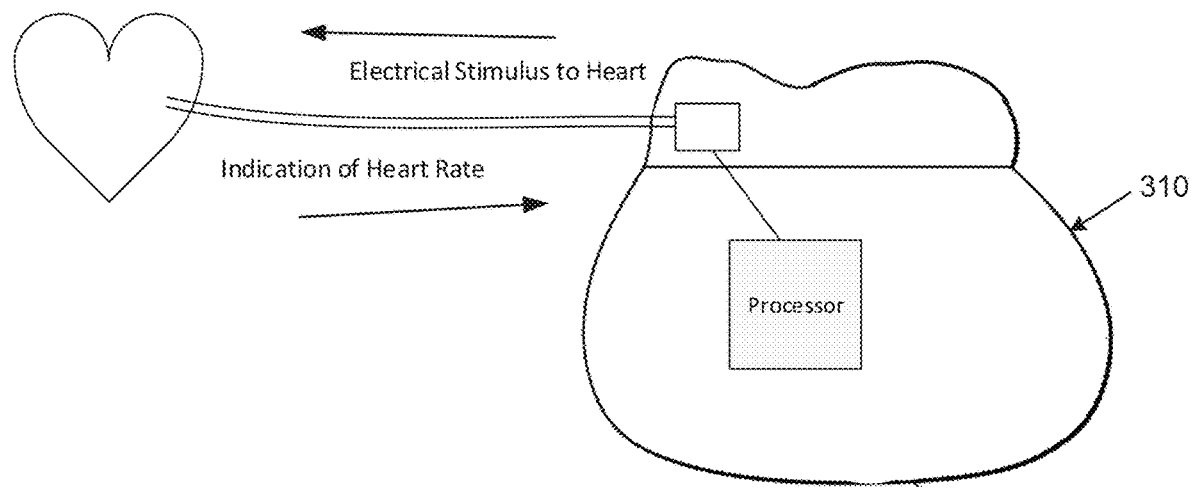
FIG. 3A depicts a pacemaker configured to detect inactivity via electrical signals from the subject's heart that are indicative of the subject's heart rate.

FIG. 3A depicts a pacemaker 310 configured to detect inactivity via electrical signals from the subject's heart that are indicative of the subject's heart rate. The processor within the pacemaker 310 may be programmed to detect inactivity of the subject based on the received signal and produce electrical stimulus to increase the subject's heart rate in response, as discussed above. In addition, the processor within the pacemaker 310 may be programmed to detect activity of the subject based on the received signal and, when it is determined that electrical stimulus is currently being produced, to cease said electrical stimulus, as discussed above.

Figure 3B:
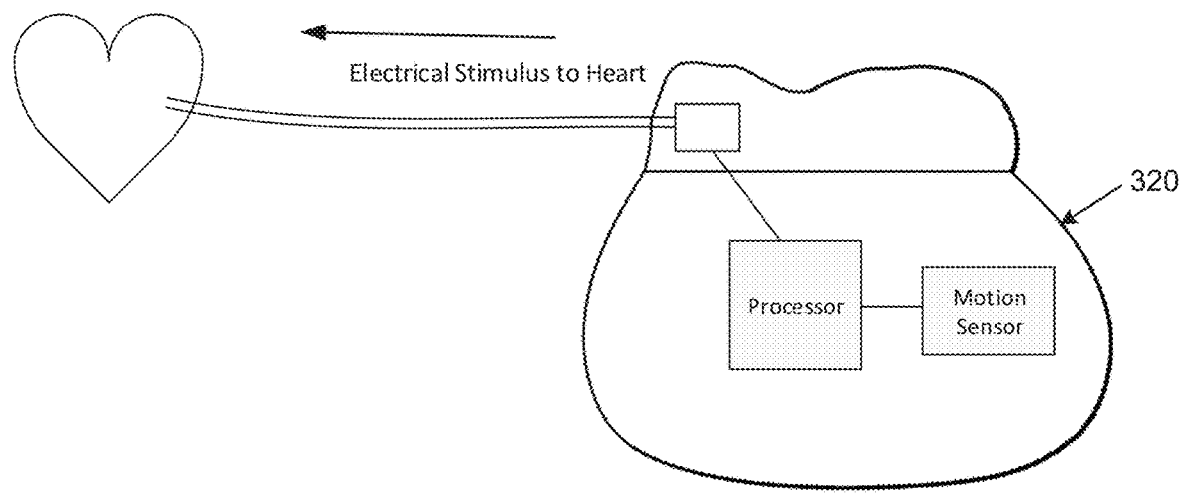
FIG. 3B depicts a pacemaker configured to detect inactivity via signals from a motion sensor situated within the pacemaker that are indicative of the subject's activity level.

FIG. 3B depicts a pacemaker 320 configured to detect inactivity via signals from a motion sensor situated within the pacemaker that are indicative of the subject's activity level. The processor within the pacemaker 320 may be programmed to detect inactivity of the subject based on a measure of the subject's motion received from the motion sensor and to produce electrical stimulus to increase the subject's heart rate in response, as discussed above. In addition, the processor within the pacemaker 320 may be programmed to detect activity of the subject based on the measure of the subject's motion received from the motion sensor and, when it is determined that electrical stimulus is currently being produced, to cease said electrical stimulus, as discussed above.

Figure 3C:
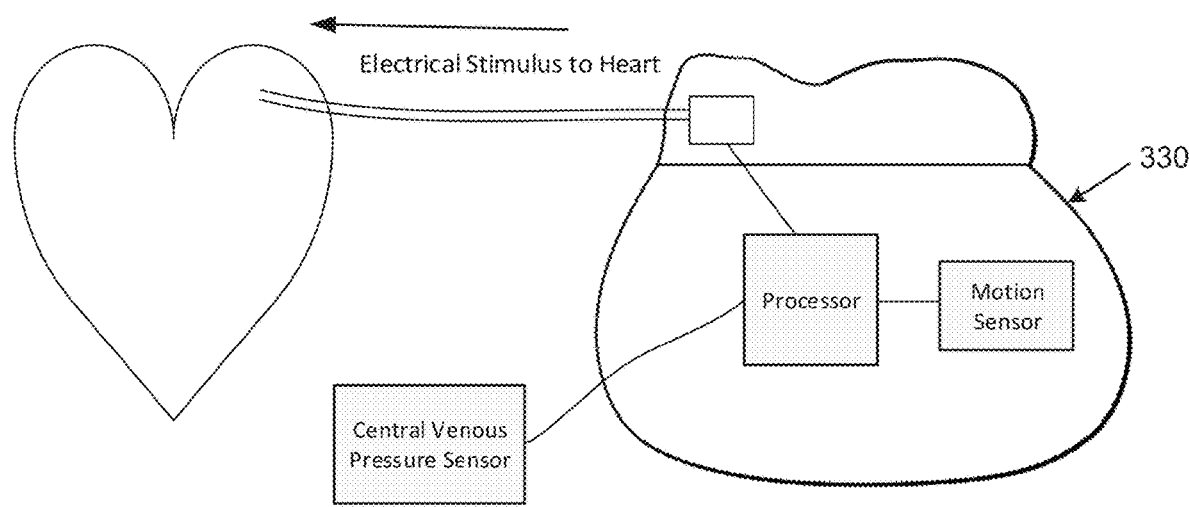
FIG. 3C depicts a pacemaker configured to detect inactivity based on signals from a motion sensor situated within the pacemaker that are indicative of the subject's activity level and/or based on signals from a central venous pressure sensor.

FIG. 3C depicts a pacemaker 330 configured to detect inactivity based on signals from a motion sensor situated within the pacemaker that are indicative of the subject's activity level and/or based on signals from a central venous pressure sensor. The central venous pressure sensor, which for instance include a central venous catheter (CVC), may be disposed at any of a number of suitable locations within the subject, such as within the jugular vein, subclavian vein, axillary vein or femoral vein. The processor within the pacemaker 320 may be programmed to detect inactivity of the subject based on either or both of the signals received from the motion sensor and the central venous pressure sensor and to produce electrical stimulus to increase the subject's heart rate in response, as discussed above. In some embodiments, a mathematical relationship may be applied by the processor of pacemaker 330 to identify whether the subject is active or inactive according to some combination of the two sensor inputs. The processor within the pacemaker 330 may be programmed to detect activity of the subject based on either or both of the signals received from the motion sensor and the central venous pressure sensor and, when it is determined that electrical stimulus is currently being produced, to cease said electrical stimulus, as discussed above.

In each of the illustrative configurations of FIGS. 3A-3C, the pacemakers 310, 320 and 330 may include one or more volatile and/or non-volatile media storing data that may be utilized in performing the techniques described herein. For instance, in embodiments in which at target heart rate is selected based on the age and/or gender of the subject, data indicative of the subject's age and/or gender may be stored in such a medium and accessed by the processor of the pacemaker when producing the electrical stimulus to the heart configured to increase the heart rate to the target rate. As an alternative, a pacemaker may be configured for a specific subject prior to the pacemaker being fitted to the subject and target heart rates for a variety of detected activity levels may be stored within the pacemaker. As such, the processor of the pacemaker need only access these target heart rates based on a detected activity level and produce appropriate electrical stimulus in response. The above are provided merely as examples, however, as numerous techniques for configuring a pacemaker to provide the above-described electrical stimulus for increasing the heart rate of a subject in response to one or more sensor inputs may be envisioned, and the invention is not limited in this respect.

Figure 4:
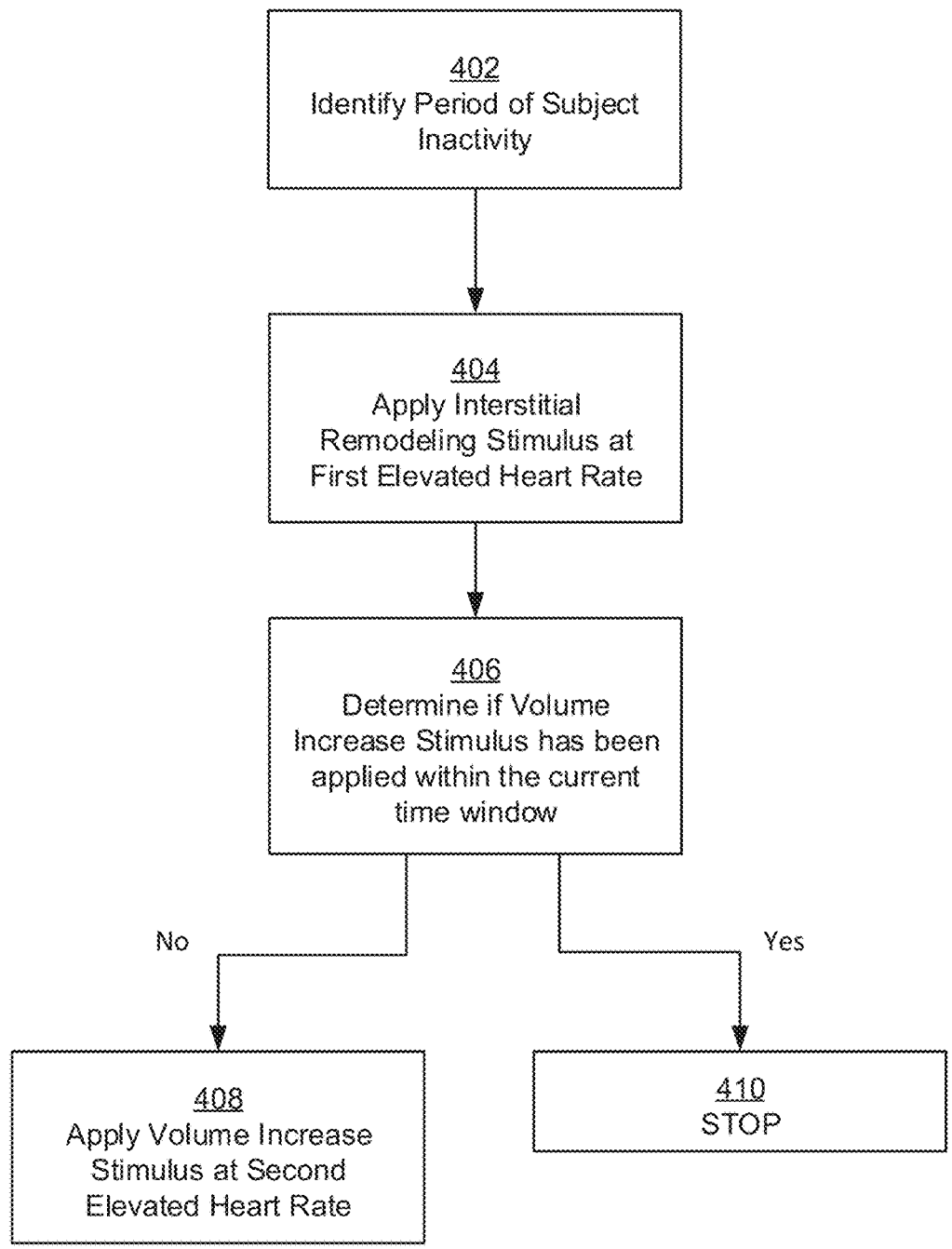
FIG. 4 is a flowchart of a method of operating a cardiac pacemaker, according to some embodiments.

FIG. 4 is a flowchart of a method of operating a cardiac pacemaker, according to some embodiments. As discussed above, the inventor has recognized and appreciated that when a subject's heart rate is raised to between 101 bpm and 140 bpm, beneficial changes to the subject's heart chamber(s) may be safely produced without discomfort in the subject. Method 400 shown in FIG. 4 is an illustrative method of producing such effects using a suitably configured pacemaker, such as pacemaker 6 shown in FIG. 1, or pacemakers 310, 320 or 330 shown in FIGS. 3A-C respectively.

Method 400 begins in act 402, in which a period of inactivity of a subject is identified. A pacemaker may be configured (e.g., via a processor and software within a pacemaker, and/or via circuitry of the pacemaker) to detect inactivity based on data received from one or more sensors. The sensors may include sensors such as sensor(s) 3 and/or 5 shown in FIG. 1, and may include one or more sensors located within the housing of the pacemaker (e.g., an accelerometer), one or more sensors located outside of the housing of the pacemaker (e.g., a heart rate detector), and/or one or more sensors located both inside and outside of the housing. The sensors may supply sensor data indicative of activity or inactivity that can be interpreted by the pacemaker in determining whether the subject is active or inactive. Said determination may include performing mathematical operations on sensor data received during a particular time window (e.g., the past 5 seconds) and comparing the result to some predetermined threshold value. Such a threshold value may depend on any number of physical characteristics of the subject, such as height, weight, age, gender, or combinations thereof. In some embodiments, data may be stored by the pacemaker (e.g., in a volatile or non-volatile memory within the pacemaker or otherwise accessible to the pacemaker) that is specific to the subject. For instance, sensor data may be gathered by observing the subject at rest and when active to calibrate the pacemaker to accurately recognize periods of inactivity.

Irrespective of how inactivity is identified in act 402, in act 404 the pacemaker applies an interstitial remodeling stimulus at a first elevated heart rate. As discussed above, an interstitial remodeling stimulus may provide physiological benefits over and above the heart remodeling benefits of increasing the heart rate to above 100 bpm. The interstitial remodeling stimulus comprises setting the pacemaker (e.g., by a processor of the pacemaker) to modulate the subject's heart at a rate higher than the subject's resting heart rate and below 100 bpm. According to some embodiments, said heart rate for interstitial remodeling stimulus may be between 70 bpm and 100 bpm, or between 80 bpm and 100 bpm, or between 90 bpm and 100 bpm, or between 95 bpm and 100 bpm, such as 99 bpm.

The interstitial remodeling stimulus may be applied for any suitable length of time, though may preferably be applied for a time period on the order of minutes, such as between 2 minutes and 15 minutes, such as between 3 minutes and 12 minutes, such as between 4 minutes and 8 minutes, such as 5 minutes.

According to some embodiments, during act 404, the pacemaker may periodically or constantly determine an activity level of the subject, and if the activity level raises above a threshold value, cease application of the interstitial remodeling stimulus. Determination of the activity level during act 404 may be based on the same or different sensor data than was used to identify inactivity in act 402, and may utilize the same or a different threshold value than was used in act 402.

Once the interstitial remodeling stimulus ends, in act 406 the pacemaker determines whether a stimulus to increase the subject's heart rate to between 101 bpm and 140 bpm, referred to herein as "volume increase stimulus," has been performed within a current window of time. In order to apply the volume increase stimulus on a regular basis but not so frequently as to potentially overstimulate the heart, method 400 is arranged to apply the volume increase stimulus not more than once within successive time windows. For instance, the time windows may be successive four hour intervals, such that method 400 will not apply the volume increase stimulus if the volume increase stimulus has already been applied within the present four hour window. The time windows may be equally sized or different sizes. For example, the time windows during nighttime hours may be comparatively shorter than daytime time windows to produce more frequent applications of the volume increase stimulus at night.

If, in act 406, it is determined that the volume increase stimulus was applied within the current time window, method 400 ends. Otherwise, method 400 proceeds to act 408 in which the volume increase stimulus is applied.

The volume increase stimulus comprises setting the pacemaker (e.g., by a processor of the pacemaker) to modulate the subject's heart at a rate above 101 bpm and below 140 bpm. Targeting a heart rate within this range has been found to be critical in order to produce beneficial remodeling of the heart without producing damage to the heart and/or discomfort to the subject. Below 101 bpm, the stimulation to the heart may be insufficient to produce beneficial remodeling of the heart. Above 140 bpm, the stimulation may produce atrial fibrillation or other detrimental effects. According to some embodiments, said heart rate for volume increase stimulus may be between 101 bpm and 140 bpm, or between 110 and 140 bpm, or between 105 bpm and 130 bpm, or between 115 bpm and 135 bpm, or between 120 bpm and 130 bpm, or between 122 bpm and 128 bpm, such as 125 bpm. According to some embodiments, the selected target heart rate may be based upon one or more physical characteristics of the subject, such as gender, age, height, weight, etc.

The volume increase stimulus may be applied for any suitable length of time, though may preferably be applied for a time period between 30 minutes and 120 minutes, such as between 40 minutes and 100 minutes, such as between 50 minutes and 80 minutes, such as 60 minutes. Each application of the volume increase stimulus may be applied for a different time period, as it may be beneficial to apply stimuli of different lengths to a subject over a given window of time. For instance, applications of the volume increase stimulus applied at night may be shorter or longer than applications of the volume increase stimulus applied during the day.

According to some embodiments, an optional step may be applied subsequent to act 408 and/or act 410. As discussed above, a pacemaker fitted to a subject may be configured to increase the subject's heart rate to a level only slight elevated above resting, which may lower central blood pressures and thereby at least some cases may mitigate issues such as atrial fibrillation. As such, an additional step of increasing the heart rate may be applied subsequent to the steps 402-408 or 402-410, where the heart rate is increased to a rate above resting but below 100 bpm. For example, after completion of the volume increase stimulus in act 408, the heart rate may be increased to above a resting rate. Alternatively, after it is determined in act 406 that the volume stimulus has been applied within the current time window, the heart rate may be increase to above a resting rate rather than allowing the heart rate to return to its natural level. In either case, the heart rate may be increased to, for instance, between 70 and 100 bpm, between 70 and 90 bpm, between 75 and 85 bpm; or between 100% and 140% of the subject's resting heart rate, or between 110% and 130% of the subject's resting heart rate, or between 115% and 130% of the subject's resting heart rate, or between 120% and 135% of the subject's resting heart rate.

The present invention is further illustrated by the following illustrative study, which is not to be construed as limiting the scope of the invention in any manner.

Illustrative Study

Results of the below-described illustrative study suggest that a moderate increase in heart rate can be used to reduce wall thickness, normalize LV chamber volumes, decrease myocardial fibrosis and/or improve LV compliance. The results also suggest that the effects of the described techniques to increase heart rate can be titrated, are reversible and do not induce heart failure. These findings may provide the rationale for a novel therapeutic approach for HFpEF and its antecedent disease substrate.

Ten adult female Yucatan Miniature swine (9 months old, 40-45 kg) were used for these studies. A pacemaker was implanted in all pigs. At the same time, a unilateral renal artery stenosis (RAS) was established in eight pigs to induce left ventricular hypertrophy. Two pigs underwent a Sham procedure without RAS.

The average intrinsic heart rate prior to the pacing intervention was 93±6/min. After two weeks of predominant atrial pacing at 150/min LV volumes markedly increased. LV end-diastolic and systolic volumes assessed in sinus rhythm increased by 54±3% and 106±23%, respectively (both p<0.01), whereas the ejection fraction fell from 58±1% to 45±1% (p<0.05). LV mass was unchanged due to wall thinning. Due to the substantial increase in LV volume and the decrease in ejection fraction after two weeks the atrial pacing rate was subsequently decreased to 125/min. Two weeks later the LV cavity size was smaller but still enlarged compared to baseline. LV end-diastolic and systolic volumes were increased by 29±24% (p=0.09) and 50±19% (p<0.01) respectively. Importantly, the ejection fraction normalized to 52±1%. Thereafter the pacing was stopped. Two weeks later the LV chamber size had returned to baseline levels prior to the pacing.

In another four animals we confirmed the effects of 125/min. The heart rate in the first three weeks prior to pacing was 88±4/min. After two weeks of pacing at 125/min the LV end-diastolic volume in sinus rhythm increased by 25±14% (p<0.05) with a trend towards an increased end-systolic volume (p=0.09). The ejection fraction was 55±1%, not different from baseline. The left ventricular mass remained unchanged as well. After cessation of pacing, LV volumes returned to baseline values within two weeks.

In six animals we were able to serially assess the LV end-diastolic pressure volume relation before and after the heart rate-induced structural change. Following two weeks of pacing at 125/min we found a rightward shift of the pressure volume relation due to the increase in chamber volume. Despite nominally lower baseline filling pressures after two weeks of pacing at 125/min this did not reach significance (p=0.24). However, diastolic compliance, expressed as $\Delta EDV/\Delta EDP$ with the volume challenge, increased from 1.95±0.72 mL/mmHg at baseline to 3.18±0.57 mL/mmHg (p<0.05) after two weeks of pacing at 125/min.

There was no significant difference in type I and III collagen levels in homogenates from RAS animals and Sham animals.

Several observations were made:

1) A moderate elevation in heart rate can increase LV volumes and lower mass-to-volume ratios in concentrically hypertrophied LVs without reducing the ejection fraction.

2) This change in LV structure is reversible, can be titrated and is not associated with heart failure.

3) The results suggest that rate-induced (re)modelling reduces myocardial fibrosis and improves diastolic compliance.

The rationale for heart rate as a treatment target originates from several physiological and clinical observations. Heart rate, through its high variability, plays a central role in cardiac workload. It is believed to play a key part in many physiological adaptations such as athlete's heart and in pregnancy. Heart rate is already an established treatment target in dilated cardiomyopathy, where a lower heart rate reduces LV chamber size. In contrast, extreme tachycardia is known to severely dilate the LV as evident in tachycardia-induced cardiomyopathy. Accordingly, we speculated that modest heart rate elevations could be used to restore chamber volumes, reduce LV wall thickness and trigger an interstitial remodeling process, which in aggregate could improve LV filling. If so, subjects with concentric hypertrophy and impaired LV filling might potentially benefit from this, if the structural remodeling can be safely accomplished.

The potential to titrate the effects of heart rate was apparent after lowering an initially-testing rate of 150/min to a rate of 125/min. The second experimental series confirmed that this reduction in LV chamber size was not merely a result of an ongoing regression of chamber volumes after pacing at 150/min but was specific to pacing at 125/min. We also determined that even a very pronounced chamber dilation induced by a heart rate of 170/min was not pathological, as determined by the lack of heart failure and biomarker elevations, and could be reversed with a rate of 125/min. Within two weeks, chamber dimensions regressed and ejection fraction normalized. These rapid structural changes demonstrate that the swiftness of the physiological cardiac remodeling process is preserved in concentric hypertrophy even when pushed to levels that exceed the physiological adaptations reported in human subjects exposed to extreme bed rest, spaceflight or reconditioning.

Although the results after pacing at rates above 125/min suggest a gradual rate-dependent decrease in ejection fraction, no clinical signs or biomarker changes suggestive of heart failure were seen at any of the studied heart rates. This suggests that the observed structural changes are within the limits of physiological adaptations without causing decompensation. This is an important finding as it is well established that pigs and other similar sized animals develop overt heart failure with increased BNP and Noradrenaline levels when exposed to rates above 200/min.

Our analysis of the end-diastolic pressure-volume relationship after pacing at 125/min demonstrates a rightward shift with a trend towards lower LV end-diastolic pressures with a substantial improvement in diastolic compliance. This may be primarily facilitated by wall thinning but a pacing-induced reduction in myocardial connective tissue could play a contributing role in this finding. Compared to non-paced RAS animals, the level of myocardial connective tissue was similarly low in both paced RAS and Sham animals. The overall very low levels of connective tissue in all paced animals were very likely the result of a concurrent interstitial matrix remodeling process that reduces collagen levels to support the elongation and thinning of individual myocytes, as shown in animal models of tachycardia-induced cardiomyopathy. Because the analyzed tissues originate from hearts that were allowed to return to their baseline geometry it is conceivable that intermittent increases in heart rate may suffice to reduce tissue fibrosis without need for a permanent chamber enlargement.

As discussed above, targeting a heart rate between 101 bpm and 140 bpm has been found to be critical in order to produce beneficial remodeling of the heart without producing damage to the heart and/or discomfort to the subject. In the above illustrative study a rate of 125 bpm was utilized, however, there is good reason to believe that similar results would be observed for other heart rates in the 101-140 bpm range. Below 100 bpm, the stimulation to the heart may be insufficient to produce beneficial remodeling of the heart. Above 140 bpm, the stimulation may produce atrial fibrillation or other detrimental effects.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Multiple elements listed with "and/or" should be construed in the same fashion, e.g., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A cardiac pacemaker for implantation within a subject, the pacemaker comprising:
   one or more electrodes;
   at least one sensor configured to detect an activity level of the subject and produce output indicative of the activity level; and
   at least one processor configured to, based on the output from the at least one sensor, perform a method of stimulating a remodeling of the subject's heart muscle through modulation of the subject's heart rate, including application of an interstitial remodeling stimulus and a volume increase stimulus, the method comprising:
   detecting that the subject is currently inactive based on the output from the at least one sensor;
   when the subject is detected to be currently inactive, applying the interstitial remodeling stimulus by causing the one or more electrodes to output a first signal configured to increase the heart rate of the subject to a first heart rate during a first time period, wherein the first heart rate is above a resting heart rate and below 100 beats per minute;
   subsequent to the interstitial remodeling stimulus ending, determining whether or not to apply the volume increase stimulus based on previous times that the cardiac pacemaker applied the volume increase stimulus; and
   when said determination is that the volume increase stimulus is to be applied, and when the first time period has elapsed, applying the volume increase stimulus by causing the one or more electrodes to output a second signal configured to increase the heart rate of the subject to a second heart rate during a second time period, wherein the second heart rate is between 100 and 140 beats per minute.

2. The cardiac pacemaker of claim 1, wherein the at least one processor is further configured to cause the one or more electrodes to:

during application of the interstitial remodeling stimulus, stop producing the first signal when the subject is detected to be currently active based on the output from the at least one sensor; and during application of the volume increase stimulus, stop producing the second signal when the subject is detected to be currently active based on the output from the at least one sensor.

3. The cardiac pacemaker of claim 1, wherein the at least one sensor includes a motion detector.

4. The cardiac pacemaker of claim 1, wherein the at least one processor is further configured to select the second heart rate based at least in part on the subject's height, weight and/or gender.

5. The cardiac pacemaker of claim 1, wherein the first heart rate is above 90 beats per minute and below 100 beats per minute.

6. The cardiac pacemaker of claim 1, wherein the first time period is a time period having a length of at least two minutes and less than ten minutes.

7. The cardiac pacemaker of claim 1, wherein the second time period is a time period having a length of at least thirty minutes and less than two hours.

8. The cardiac pacemaker of claim 7, wherein the second time period is a time period of approximately one hour.

9. The cardiac pacemaker of claim 1, wherein the second heart rate is between 110 and 140 beats per minute.

10. The cardiac pacemaker of claim 1, wherein said determining whether or not to apply the volume increase stimulus is based on the previous times and durations that the cardiac pacemaker applied the volume increase stimulus.

11. The cardiac pacemaker of claim 10, wherein said determining that the volume increase stimulus is to be applied is made when the previous times that the cardiac pacemaker applied the volume increase stimulus indicates that the volume increase stimulus was not applied within a past window of time.

12. The cardiac pacemaker of claim 11, wherein the past window of time is a past time window of four hours.

13. The cardiac pacemaker of claim 1, further comprising a housing, the at least one processor being arranged within the housing.

* * * * *